(12) United States Patent
Gujral et al.

(10) Patent No.: US 11,242,320 B2
(45) Date of Patent: Feb. 8, 2022

(54) PROCESS FOR THE PREPARATION OF PYRACLOSTROBIN

(71) Applicant: GSP CROP SCIENCE PVT. LTD., Ahmedabad (IN)

(72) Inventors: Ajit Singh Gujral, Ahmedabad (IN); Kenal V. Shah, Ahmedabad (IN); Bhavesh V. Shah, Ahmedabad (IN); Subhash Rajaram Kadam, Ahmedabad (IN); Nilesh N. Jani, Ahmedabad (IN); Ravindra Y. Shinde, Ahmedabad (IN)

(73) Assignee: GSP CROP SCIENCE PVT. LTD., Ahmedabad (IN)

( * ) Notice: Subject to any disclaimer, the term of this patent is extended or adjusted under 35 U.S.C. 154(b) by 0 days.

(21) Appl. No.: 16/962,542

(22) PCT Filed: Jan. 16, 2019

(86) PCT No.: PCT/IB2019/050332
§ 371 (c)(1),
(2) Date: Jul. 16, 2020

(87) PCT Pub. No.: WO2019/142107
PCT Pub. Date: Jul. 25, 2019

(65) Prior Publication Data
US 2020/0354322 A1    Nov. 12, 2020

(30) Foreign Application Priority Data
Jan. 17, 2018  (IN) .............................. 201821001941

(51) Int. Cl.
C07D 231/22    (2006.01)

(52) U.S. Cl.
CPC .................................. *C07D 231/22* (2013.01)

(58) Field of Classification Search
CPC ..................................................... C07D 231/22
See application file for complete search history.

(56) References Cited

U.S. PATENT DOCUMENTS 8,563,748 B2    10/2013    Korte et al.

FOREIGN PATENT DOCUMENTS

| CN | 104211641 A | 12/2014 | |
| WO | WO-2017025377 A1 * | 2/2017 | ........... C07D 231/04 |

OTHER PUBLICATIONS

PCT Search Report dated Apr. 15, 2019, Application No. PCT/IB2019/050332.
PCT Written Opinion dated Apr. 15, 2019, Application No. PCT/IB2019/050332.

* cited by examiner

*Primary Examiner* — Shawquia Jackson
(74) *Attorney, Agent, or Firm* — The Dobrusin Law Firm, P.C.; Bryan S. Lemanski

(57) ABSTRACT

The present invention relates to a novel and improved process for preparation of methyl [2-({[1-(4-chlorophenyl)-1H-pyrazol-3-yl]oxy}methyl)phenyl]methoxycarbamate (Pyraclostrobin) of formula (I) in free form or in agrochemically acceptable salt form useful as a pest control agent starting from methyl [2-({[1-(4-chlorophenyl)-1-H-pyrazol-3-yl]oxy}methyl)phenyl]hydroxycarbamate in simple manner and in high purity and good yield.

7 Claims, No Drawings

PROCESS FOR THE PREPARATION OF PYRACLOSTROBIN

FIELD OF THE INVENTION

The present invention relates to a novel and improved process for the preparation of methyl [2-({[1-(4-chlorophenyl)-1H-pyrazol-3-yl] oxy} methyl) phenyl]methoxycarbamate of formula (I) in free form or in agrochemically acceptable salt form useful as a pest control agent.

Formula-I

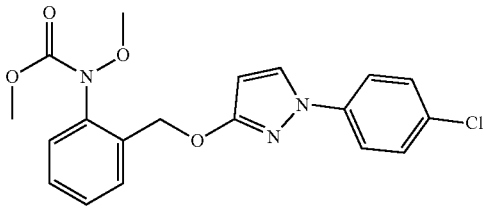

methyl [2-({[1-(4-chlorophenyl)-1H-pyrazol-3-yl]
oxy}methyl)phenyl]methoxycarbamate
$C_{19}H_{18}ClN_3O_4$
Mol. Wt.: 387.82

BACKGROUND OF THE INVENTION

Pyraclostrobin, compound of formula (I) is a strobilurin fungicide developed by BASF. Because of its low toxicity and low efficiency, chemically stable, broad spectrum bactericidal and pesticide properties it can be used in a variety of crops such as rice, wheat, peanuts, fruit trees, powdery mildew, downy mildew sheath blight, gray mold, leaf spot and other wide range of diseases have a strong preventive effect.

It controls major plant pathogens, such as *Septoriatritici, Puccinia* spp., *Drechslera tritici-repentis* and *Pyrenophora teres* in cereals, *Mycosphaerella* spp. in peanuts, *Septoria glycines, Cercospora kikuchii* and *Phakopsora pachyrhizi* in soya beans, *Plasmopara viticola* and *Uncinula necator* in grapes, *Phytophthora infestans* and *Alternaria solani* in potatoes and tomatoes, *Mycosphaerella fijiensisin* bananas, *Elsinoë fawcettii* and *Guignardia citricarpa* in citrus, and *Rhizoctonia solani* and *Pythiumaphani dermatum* in turf. Application rates c. 50-250 g/ha for food crops and 280-560 g/ha for turf.

Pyraclostrobin is synthesized by mainly two routes. Patents/Publications such as U.S. Pat. No. 5,869,517, WO1996/001256, IN242743 (1679/MAS/1995), EP0624155B1, WO1996/001256 discloses the route, which uses o-nitrotoluene as starting material. In this process o-nitrotoluene is hydrogenated to give 2-hydroxylamine toluene, followed by acetylation, methylation and bromination to give N-[2-(bromomethyl) phenyl]-N-methoxy-methyl. It is then treated with 1-(4-chlorophenyl)-pyrazol-3-ol to give the desired product Pyraclostrobin having formula (I).

This patent route was developed for the preparation of Pyraclostrobin. Due to some criticality of the process still it is a manufacturing process. In this patent the process hydrogenation of o-nitro toluene gives N-hydroxy-2-methylaniline. But in this step there is a problem to control the reaction at the desired stage and it is very difficult. In Methylation step, Methyl Iodide is used as the methylating agent. It is too costly. So commercially it is not a viable process. In methylation step if dimethyl sulfate is used as a methylating agent, it will increase the effluent load. In brominating step dibromide impurity formation occurs, so there is required purification to obtain Pyraclostrobin and it is very difficult.

Patents No. U.S. Pat. No. 8,816,096B2, WO2012038392, WO2012120029, CN102399190, CN104211641, CN105218450, CN104592117, CN106117143, CN105949125 disclose another route, in which 2-nitrobenzyl bromide is reacted with 1-(4-chlorophenyl)-1H-Pyrazol-3-ol to give 1-(4-chlorophenyl)-3-[(2-nitrobenzyl)oxy]-1H-pyrazole, and then the nitro group is reduced to hydroxylamine, after acetylation and methylation to give the desired product. While this patented process successfully prepared Pyraclostrobin, hydrogenation of nitro group to hydroxylamine is difficult to control. The reaction does not stop at this stage and there is a generation of hydroxylamine impurity. In Methylation, Dimethyl sulfate is used as a methylating agent so ultimately it increases the effluent load.

In another route 2-nitro-benzyl bromide was reacted with pyrrolidine N-(2-nitrobenzyl) pyrrolidine, and then the nitro group is reduced to hydroxylamine, followed by acetylation, and methylation to obtain protected pyrrole N-[2-(chloromethyl) phenyl]-N-methoxy-methyl, it then treated with 1-(4-chlorophenyl) pyrazol-3-ol to give Pyraclostrobin having Formula (I).

In this patented process Pyraclostrobin can be prepared successfully, but in the preparation process hydrogenation of nitro group to hydroxylamine is difficult to control and there is the generation of hydroxylamine impurity. In methylation step, Methyl iodide is used as methylation agent. It is too costly. So commercially it is not a viable process. In this patented process due to protection and deprotection of groups, the process becomes longer as well as results in low productivity in existing plant setup.

CN104592117A discloses methylation of methyl [2-({[1-(4-chlorophenyl)-1-H-pyrazol-3-yl]oxy}methyl)phenyl]hydroxycarbamate by using methylating agent Dimethyl Sulfate in presence of a base. Reaction carried out in presence of a solvent Dichloroethane and N,N-dimethyl formamide alone or a mixture of both to get Pyraclostrobin. This process used Dimethyl Sulfate as a methylating agent which will ultimately increase the effluent load.

CN104211641A discloses methylation of methyl [2-({[1-(4-chlorophenyl)-1-H-pyrazol-3-yl]oxy}methyl)phenyl]hydroxycarbamate by using methylating agent Dimethyl Sulfate or Dimethyl Carbonate in presence of a base such as sodium hydroxide, potassium hydroxide, sodium carbonate, potassium carbonate to give Pyraclostrobin having the formula (I). Reaction carried out in presence of solvents such as Toluene, O-Xylene, and Dichloroethane. This process used Dimethyl Sulfate or Dimethyl Carbonate as a methylating agent which will ultimately increase the effluent load.

CN102399190A discloses methylation of methyl [2-({[1-(4-chlorophenyl)-1-H-pyrazol-3-yl]oxy}methyl)phenyl]hydroxycarbamate by using Dimethyl sulfate as a methylating agent in the presence of acid-binding agent and solvents used like polar solvent or a non-polar solvent to give Pyraclostrobin. The use of Dimethyl Sulfate as methylating agent increases the effluent load.

In this process polar solvent used is ketone viz acetone, methyl ethyl ketone, isobutyl ketone, amyl ketone, methyl isobutyl ketone or arbitrarily mixing the two non-polar solvent or chlorinated alkanes any two of dichloromethane, chloroform, carbon tetrachloride, dichloroethane 1,2_, 1,1_ a dichloroethane mix.

The present inventors have found that by the process of the present invention Pyraclostrobin is obtained in high purity and good yield. The present inventors have found that the process of the present invention involves minimum time and maximum conversion of methyl [2-({[1-(4-chlorophenyl)-1-H-pyrazol-3-yl]oxy}methyl)phenyl]hydroxycarbamate, compound of formula II into Pyraclostrobin, compound of formula (I) and therefore productivity is more. The product can be crystallized in suitable solvents to get Pyraclostrobin in uniform crystalline form.

OBJECTS OF THE INVENTION

It is an object of the present invention to provide an improved process for the preparation of methyl [2-({[1-(4-chlorophenyl)-1H-pyrazol-3-yl] oxy} methyl) phenyl] methoxycarbamate (Pyraclostrobin) of formula (I) in free form or in agrochemically acceptable salt form starting from methyl [2-({[1-(4-chlorophenyl)-1-H-pyrazol-3-yl]oxy}methyl)phenyl]hydroxycarbamate in simple manner and in high purity and good yield.

SUMMARY OF THE INVENTION

According to an aspect of the present invention there is provided an improved process for the preparation of methyl [2-({[1-(4-chlorophenyl)-1H-pyrazol-3-yl] oxy} methyl) phenyl] methoxycarbamate (Pyraclostrobin) of formula (I)

Formula(I)

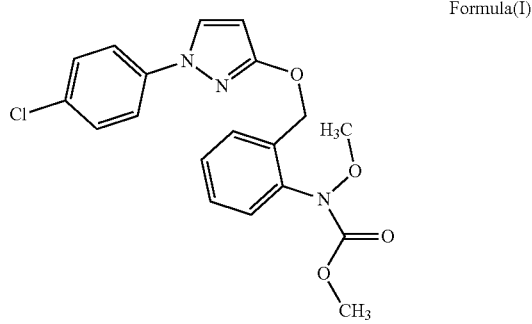 [SMILES: COC(=O)N(OC)c1ccccc1COc1ccn(-c2ccc(Cl)cc2)n1]

comprising the steps of:
i) Reacting compound of formula (II) with methylating agent selected from Methyl Chloride or Methyl bromide in presence of a catalyst and acid binding agent in solvent or mixture of solvents, optionally in presence of phase transfer catalyst at a reaction temperature between 30°-50° C. under pressure between 1.0 to 10.0 $Kg/cm^2$ to obtain crude Pyraclostrobin, compound of formula (I);

ii) Purifying Crude Pyraclostrobin of formula (I) obtained in step (i) in suitable solvent or mixture of solvents.

DETAILED DESCRIPTION OF THE INVENTION

The present invention provides a novel and improved process for the preparation of methyl [2-({[1-(4-chlorophenyl)-1H-pyrazol-3-yl] oxy} methyl) phenyl]methoxycarbamate (Pyraclostrobin) of formula (I) having structural formula given below.

Formula-I

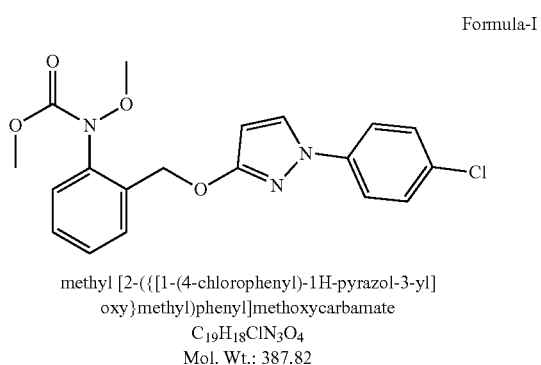 [SMILES: COC(=O)N(OC)c1ccccc1COc1ccn(-c2ccc(Cl)cc2)n1]

methyl [2-({[1-(4-chlorophenyl)-1H-pyrazol-3-yl]oxy}methyl)phenyl]methoxycarbamate
$C_{19}H_{18}ClN_3O_4$
Mol. Wt.: 387.82

The present invention provides a simple, economically viable and efficient process for preparing a methyl [2-({[1-(4-chlorophenyl)-1H-pyrazol-3-yl] oxy} methyl) phenyl] methoxycarbamate (Pyraclostrobin) of formula (I).

The invention will now be described in various aspects thereof and may be more fully understood and appreciated and briefly described as follows.

In one of the embodiment the present invention provides a novel and improved process for the preparation methyl [2-({[1-(4-chlorophenyl)-1H-pyrazol-3-yl] oxy} methyl) phenyl] methoxycarbamate (Pyraclostrobin) of formula (I) by methylation of methyl [2-({[1-(4-chlorophenyl)-1-H-pyrazol-3-yl]oxy}methyl)phenyl]hydroxycarbamate having formula (II) using methylating agent selected from Methyl Chloride or Methyl bromide in presence of catalyst and acid binding agent in solvent or mixture of solvents optionally in presence of phase transfer catalyst.

Formula(II)

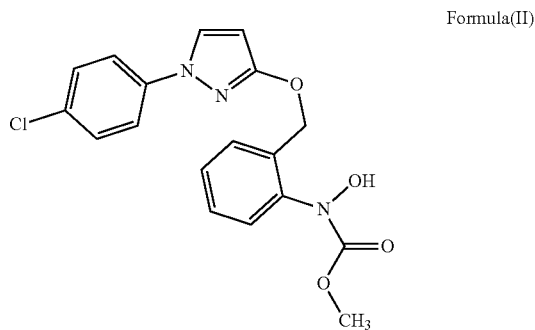 [SMILES: COC(=O)N(O)c1ccccc1COc1ccn(-c2ccc(Cl)cc2)n1]

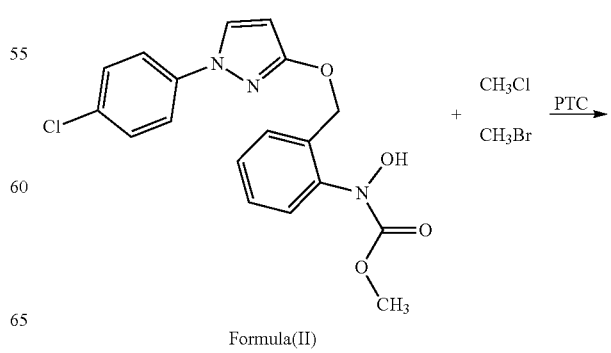

Formula(II)

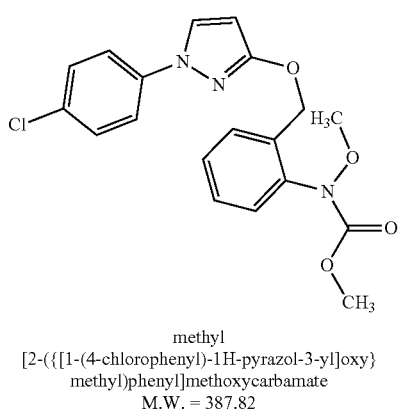

methyl
[2-({[1-(4-chlorophenyl)-1H-pyrazol-3-yl]oxy}
methyl)phenyl]methoxycarbamate
M.W. = 387.82

Mole ratio of methylating agent used for methylation reaction to methyl[2-({[1-(4-chlorophenyl)-1-H-pyrazol-3-yl]oxy}methyl)phenyl] hydroxycarbamate is in the range of 1~5.0.

Catalyst used in step (i) is Potassium Iodide and the ratio is 0.2 to 2.0% w/w on the basis of methyl [2-({[1-(4-chlorophenyl)-1-H-pyrazol-3-yl] oxy}methyl) phenyl]hydroxycarbamate.

In an embodiment the process for the preparation of methyl [2-({[1-(4-chlorophenyl)-1H-pyrazol-3-yl] oxy}methyl) phenyl] methoxycarbamate (Pyraclostrobin) of formula I by methylation of methyl[2-({[1-(4-chlorophenyl)-1-H-pyrazol-3-yl]oxy}methyl)phenyl]hydroxycarbamate having formula (II) is carried out using methyl chloride gas in presence of polar protic solvent or chlorinated solvent or ether or mixture thereof and acid binding agent such as Potassium Carbonate, Sodium Carbonate, Sodium Hydroxide or Potassium Hydroxide especially potassium Carbonate. Methylation optionally may be carried out in presence of phase transfer catalyst such as tetrabutyl ammonium bromide, tetraethyl ammonium bromide, trimethyl butyl ammonium bromide, cetyl trimethyl ammonium bromide, Polyether compound such as polyethylene glycol 400, polyethylene glycol 600 or polyethylene glycol 800 or mixtures thereof.

In the process of the present invention solvents are selected from polar solvent such as ketones, acetone, methyl ethyl ketone, isobutyl ketone, amyl ketone, methyl isobutyl ketone or chlorinated alkanes such as dichloromethane, chloroform, carbon tetrachloride, dichloroethane 1,2_, 1,1_a dichloroethane mix or methyl tert-butyl ether (MTBE) or mixture thereof such as mixture of any two solvents.

In another embodiment the process for the preparation of methyl [2-({[1-(4-chlorophenyl)-1H-pyrazol-3-yl] oxy}methyl) phenyl]methoxycarbamate (Pyraclostrobin) of formula (I) by methylation of methyl[2-({[1-(4-chlorophenyl)-1-H-pyrazol-3-yl]oxy}methyl)phenyl]hydroxycarbamate having formula (II) is carried out using methyl bromide gas in presence of polar protic solvent or chlorinated solvent or ether or mixture thereof and acid binding agent such as Potassium Carbonate, Sodium Carbonate, Sodium Hydroxide and Potassium Hydroxide especially potassium Carbonate wherein the organic solvent used in this step is selected from polar protic solvent such as ketones, acetone, methyl ethyl ketone, isobutyl ketone, amyl ketone, methyl isobutyl ketone or chlorinated alkanes such as dichloromethane, chloroform, carbon tetrachloride, dichloroethane 1,2_, 1,1_ a dichloroethane mix or methyl tert-butyl ether (MTBE) or mixture thereof such as mixture of any two solvents. Methylation optionally may be carried out in presence of phase transfer catalyst such as tetrabutyl ammonium bromide, tetraethyl ammonium bromide, trimethyl butyl ammonium bromide, cetyl trimethyl ammonium bromide, Polyether compound such as polyethylene glycol 400, polyethylene glycol 600 or polyethylene glycol 800 or mixtures thereof.

Acid binding agent used in the present invention is selected from the group consisting of Potassium Carbonate, Sodium Carbonate, Sodium Hydroxide and Potassium Hydroxide, preferably potassium Carbonate. Mole Ratio of the acid binding agent to methyl [2-({[1-(4-chlorophenyl)-1-H-pyrazol-3-yl] oxy}methyl)phenyl] hydroxycarbamate is in range of 13.0. Methylation was carried out in presence of phase transfer catalyst selected from tetrabutyl ammonium bromide, tetraethyl ammonium bromide, trimethyl butyl ammonium bromide, cetyl trimethyl ammonium bromide, polyether compound such as polyethylene glycol 400, polyethylene glycol 600 or polyethylene glycol 800 or mixtures thereof.

The present invention relates to methylation of "methyl [2-({[1-(4-chlorophenyl)-1-H-pyrazol-3-yl]oxy}methyl) phenyl]hydroxycarbamate", of formula (II) to produce, methyl [2-({[1-(4-chlorophenyl)-1H-pyrazol-3-yl] oxy} methyl) phenyl] methoxycarbamate sometimes hereinafter referred to as "Pyraclostrobin". In previous patents mentioned above disclosed that the methylation of methyl [2-({ [1-(4-chlorophenyl)-1-H-pyrazol-3-yl]oxy}methyl)phenyl] hydroxycarbamate is carried in an alkaline medium with Dimethyl sulfate (DMSO4) to produce Pyraclostrobin which is a fungicide of outstanding activity.

The present inventors found that to put the use of Methyl Chloride/Methyl Bromide into commercial practice for methylation of methyl [2-({[1-(4-chlorophenyl)-1-H-pyrazol-3-yl]oxy}methyl)phenyl]hydroxycarbamate, the best method by which it can be effected is by conducting the reaction in a closed vessel and removing all air prior to introduction of the methyl chloride/methyl bromide. There is advantageously employed a valve controlling the introduction of the methyl chloride/methyl bromide so that the pressure in the gas space cannot rise above about 6.0 Kg·cm$^2$ i.e. when the pressure rises to that level the valve is closed and methyl chloride/methyl bromide supply is interrupted. In the course of time the methyl chloride/methyl bromide reacts and the pressure therefore drops, whereupon methyl chloride/methyl bromide supply is resumed. During the major portion of the reaction, the pressure is below 3 Kg/cm$^2$. The autogenic pressure drops and the stoichiometric quantity of methyl chloride or methyl bromide measured through the tone dry in secondary pressure gauge fitted to the autoclave. This eliminates waste while at the same time simplifying the process. Higher pressures than atmospheric pressure could similarly be employed with corresponding controls for the methyl chloride/methyl bromide feed. The reaction itself is conducted in an alkaline medium, i.e. at a pH of about 10 to 12. Any alkali can be employed such as alkali metal hydroxides and/or carbonates. Alkali carbonates are preferred as acid scavengers.

There must of course at least be sufficient alkali present to react with the methyl [2-({[1-(4-chlorophenyl)-1-H-pyrazol-3-yl]oxy}methyl)phenyl]hydroxycarbamate of formula (II) and form the Metal salt, for example, and sufficient solvent in reaction mass of methyl [2-({[1-(4-chlorophenyl)-1-H-pyrazol-3yl]oxy}methyl)phenyl]hydroxycarbamate salt. The temperature is not critical and may range from about 30 to 60° C. and preferably about 30° to 55° C. The reaction is carried under pressure between 1.0 to 10.0 Kg/cm², preferably 1.0 to 5.0 Kg/cm². The reaction time depends upon the other parameters but can be reduced by one-half or more by use of a phase transfer catalyst, e.g. Phase Transfer Catalysts used such as tetrabutyl ammonium bromide, tetraethyl ammonium bromide, trimethyl butyl ammonium bromide, cetyl trimethyl ammonium bromide, Polyether compound such as polyethylene glycol 400, polyethylene glycol 600 or polyethylene glycol 800 or DABCO. Ratio of Phase Transfer Catalyst is 0.5% to 10% by mass. The ratio of phase transfer catalyst to methyl [2-({[1-(4-chlorophenyl)-1-H-pyrazol-3-yl]oxy}methyl) phenyl] hydroxycarbamate is in the range of 0.2 to 2.0% w/w basis. In such a system there is desirably considerable agitation to speed up the reaction and even a recirculation pump.

Advantageously the methyl bromide/methyl chloride point of introduction into the system is through a drip opening into the outlet line i.e. pressure side of the recirculation pump so as to effect rapid distribution and reaction. Other means are to add the methyl chloride/methyl bromide to the top of a fast running agitator. After all the methyl chloride/methyl bromide supply has been discontinued it is advantageous to hold the mass at reaction temperature for about an hour. Advantageously the reaction is effected in a system comprising a reactor vessel. At the end of the reaction in the reactor, nitrogen gas under pressure is supplied as a purge and nitrogen together with any vapors passes through a dip-tube into the dissolving vessel which contains methyl [2-({[1-(4-chlorophenyl)-1-H-pyrazol-3-yl]oxy}methyl)phenyl]hydroxycarbamate of formula (II) in the solution. This consumes the toxic methyl chloride/methyl bromide vapors without losing them from the process. Alternatively, but less desirable, the vapors can be absorbed, as on charcoal, and later desorbed for recycling to another methylation cycle. Liquid absorption can also be employed as well as direct passage to the dissolving vessel without nitrogen but using a vacuum or a pump to effect the transfer. The contents of the reactor are filtered or centrifuged to remove the salt. Mother liquor contains product taken for isolation of the product Pyraclostrobin. Salt contains sodium chloride or sodium bromide. Principally sodium bromide is reacted with sulfuric acid and methanol in a known manner to regenerate methyl bromide or sodium chloride reacted with sulfuric acid and methanol in a known manner to regenerate methyl chloride for use in the described invention. Alternatively, they may be partially concentrated and similarly treated but this is less desirable because of a lower overall methyl chloride or methyl bromide recovery. The crude Pyraclostrobin product obtained by the process is purified in suitable solvents selected from Polyethylene glycol (PEG), Isopropyl Alcohol, hexane or mixture thereof. The invention will be further described in the following illustrative examples wherein all parts are by weight unless otherwise expressed.

The yield of Pyraclostrobin obtained by the present invention is in the range from 86%-99% and purity is in the range from 94%-99%.

The above process can be represented stepwise as shown below:

REACTION SCHEME

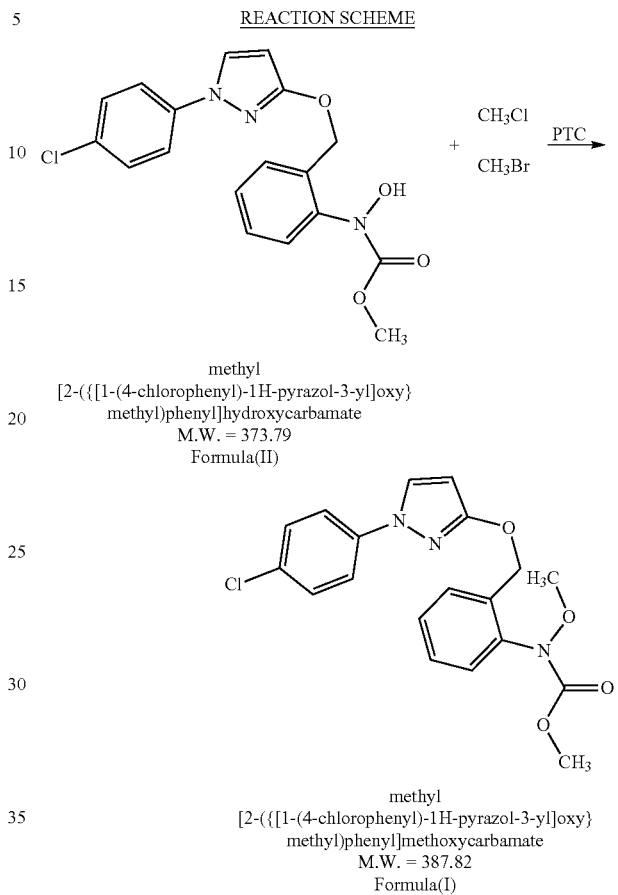

methyl [2-({[1-(4-chlorophenyl)-1H-pyrazol-3-yl]oxy}methyl)phenyl]hydroxycarbamate
M.W. = 373.79
Formula(II)

methyl [2-({[1-(4-chlorophenyl)-1H-pyrazol-3-yl]oxy}methyl)phenyl]methoxycarbamate
M.W. = 387.82
Formula(I)

The process of the present invention is illustrated with reference to the following Examples and is not intended to limit the scope of the invention. Any permutations and modifications in the process are possible keeping in mind the scope of the invention.

EXAMPLE 1

To carry out the process for the preparation of Pyraclostrobin there are employed two vessels, one serving as a dissolving vessel and the other as an autoclave reactor. The autoclave vessel is charged with, 300 ml Acetone, 25 gm of, "methyl [2-({[1-(4-chlorophenyl)-1-H-pyrazol-3-yl]oxy}methyl)phenyl] hydroxycarbamate", 0.25 gm of Potassium Iodide, and 18.5 gm of $K_2CO_3$. The vessel is agitated. Purged methyl bromide gas to the reactor at such a rate that temperature of the reactor should be maintained 30 to 50° C. After completion of the alkylation reaction, the excess of methyl bromide gas is transferred from the autoclave reactor into the dissolving vessel, by a nitrogen purge. Specifically, the reactor is pressurized with nitrogen and then a valve between the said two vessels is opened to allow the nitrogen/methyl bromide gas mixture to be purged via a dip pipe into the dissolver. The reactor is purged for 30 minutes with a nitrogen stream until all methyl bromide is removed. Removal of all methyl bromide is essential because of the high toxicity of methyl bromide. The mixture is thereafter tested for complete removal of methyl bromide before the product slurry is discharged to the filtration equipment.

Before any Methyl Bromide is Added to the Reactor the Following Operations are Performed:

The reactor is evacuated by means of a vacuum pump and the pressure inside the vessel is reduced to 100 millibars. After disconnecting the vacuum pump, the charging of the methyl bromide is started. The methyl bromide is injected into the return line of the recirculation pipe shortly behind the outlet of the pressure side of the pump. The temperature in the reaction vessel is kept at 25-50° C. by cooling. Methyl bromide is charged into the reactor at a rate of 2.0 kg per hour. A valve interrupts methyl bromide addition if the pressure in the alkylation reactor exceeds 4.0 Kg/cm$^2$. As soon as the reaction is finished excess methyl bromide builds up a pressure inside the vessel is up to 5.0 Kg/cm$^2$ that quickly reaches the set-point so the methyl bromide supply is shut off. In this way, it is not necessary to control the amount of methyl bromide by a weighing procedure because the addition is terminated by the excess of the alkylation reagent building high pressure to reach the set-point so the methyl bromide supply is terminated. Furthermore always having a small negative pressure inside the alkylation reactor (except upon completion of the alkylation) reduces the possibility of methyl bromide leaks into the plant area. After the addition of the methyl bromide usually, post-reaction is carried on for 3.0 to 4.0 hours. To remove the excess methyl bromide present in the alkylation reactor, the vessel is pressurized with nitrogen up to 5.0 bars and a vent line to the solution vessel is opened. The excess methyl bromide is now stripped from the product slurry in the reactor into the solution vessel, in the meantime reactor has been charged with a new methyl [2-({[1-(4-chlorophenyl)-1-H-pyrazol-3-yl]oxy}methyl) phenyl]hydroxycarbamate. The solution tank is equipped with a gas condenser, where escaping methyl bromide is condensed from the nitrogen stream, which is finally fed into a waste air incineration unit. The nitrogen purge is continued for 30 minutes; after this period the slurry from the reactor is discharged to an agitated pressure nutsche filter or a centrifuge and salt is separated from the mother liquor.

Recovered solvent from the mother liquor and the product extracted in 100 ml Dichloromethane or Dichloromethane and given 100 ml water wash to the organic layer. After water washing recovered solvent from the organic layer. (26.5 gm) crude Pyraclostrobin was obtained. Crude Pyraclostrobin then crystallized in a suitable solvent like Isopropyl Alcohol and hexane mixture (2.5:97.5) to get the Pyraclostrobin (25.58 gm) having w/w % Purity=98.2% and Yield=98.60%.

EXAMPLE 2

250 g of methyl [2-({[1-(4-chlorophenyl)-1-H-pyrazol-3-yl]oxy}methyl)phenyl]hydroxycarbamate is charged in 750 ml of Acetone. Then added 138 gm of Potassium Carbonate, 2.5 g of the Potassium Iodide is added; then the reaction flask is evacuated and with strong agitation, 73 g of methyl bromide is added as fast as possible at a temperature between 30°-50° C. Thereafter in 32 minutes, the required amount is absorbed. Maintained reaction mixture for 3.0 to 4.0 hrs at a reaction temperature of 30°-50° C. under 3.0 to 5.0 Kg/cm$^2$ pressure. Thereafter the slurry is cooled to 25°-30° C. and the salt precipitate is isolated by filtration. Recovered solvent from mother liquor and product extracted in 100 ml Dichloromethane and given 100 ml water wash to the organic layer. After water washing recovered solvent from the organic layer to get 265 gm crude Pyraclostrobin. Crude Pyraclostrobin then crystallized in a suitable solvent like Polyethylene glycol PEG:Isopropyl Alcohol:hexane mixture (1:3:97) to get the Pyraclostrobin 256 gm Pyraclostrobin having w/w % Purity=98.2% and yield=98.69%.

EXAMPLE 3

250 g of methyl [2-({[1-(4-chlorophenyl)-1-H-pyrazol-3-yl]oxy}methyl)phenyl]hydroxycarbamate is charged in 750 ml of Acetone. Then added 185 gm of Potassium Carbonate, 2.4 g of the Potassium Iodide is added; then the reaction flask is evacuated and with strong agitation, 41 g of methyl chloride is added as fast as possible at a temperature between 30°-50° C. Thereafter in about 32 minutes the required amount is absorbed. Maintained reaction mixture for 3.0 to 4.0 hrs at a reaction temperature of 30°-50° C. under 3.0 to 5.0 Kg/cm$^2$ pressure. Thereafter the slurry is cooled to 25°-30° C. and the salt precipitate is isolated by filtration. Recovered solvent from mother liquor and product extracted in 100 ml Dichloromethane and given 100 ml water wash to the organic layer. After water washing recovered solvent from the organic layer to get crude Pyraclostrobin. Crude Pyraclostrobin then crystallized in suitable solvent like Isopropyl Alcohol and hexane mixture (4:96) to get 255.5 gm Pyraclostrobin having w/w % Purity=98.5% and Yield=98.50

EXAMPLE 4

250 g of methyl [2-({[1-(4-chlorophenyl)-1-H-pyrazol-3-yl]oxy}methyl)phenyl]hydroxycarbamate is charged in 300 ml of Methyl Isobutyl Ketone. Then added 138 gm of Potassium Carbonate, 2.5 g of the Potassium Iodide is added; then the reaction flask is evacuated and with strong agitation, 45 g of methyl chloride is added as fast as possible at a temperature between 30°-50° C. Thereafter in about 32 minutes the required amount is absorbed. Maintained reaction mixture for 6.0 to 8.0 hrs at a reaction temperature in between 30°-50° C. under 3.0 to 5.0 Kg/cm$^2$ pressure. Thereafter the slurry is cooled to 25°-30° C. and the salt precipitate is isolated by filtration. Filtrate washes with 100 ml water. After water washing recovered solvent from the organic layer to get Crude Pyraclostrobin. Crude Pyraclostrobin then crystallized in suitable solvent like Isopropyl Alcohol and hexane mixture (5:95) to get the 249.78 gm Pyraclostrobin having w/w % Purity=98.45% Yield=96.3%

EXAMPLE 5

250 g of methyl [2-({[1-(4-chlorophenyl)-1-H-pyrazol-3-yl]oxy}methyl)phenyl]hydroxycarbamate is charged in 750 ml of Methyl Isobutyl Ketone. Then added 140 gm of Potassium Carbonate, 1.5 g of the Potassium Iodide is added; then the reaction flask is evacuated and with strong agitation, 75 g of methyl bromide is added as fast as possible at a temperature between 30°-50° C. Thereafter in about 32 minutes the required amount is absorbed. Maintained reaction mixture for 10 to 12.0 hrs at a reaction temperature in between 30°-50° C. under 3.0 to 5.0 Kg/cm$^2$ pressure. Thereafter the slurry is cooled to 25°-30° C. and the salt precipitate is isolated by filtration. Recovered solvent from the mother liquor and the product extracted in 100 ml Dichloromethane or Dichloromethane and given 100 ml water wash to the organic layer. After water washing recovered solvent from the organic layer to get crude Pyraclostrobin. Crude Pyraclostrobin then crystallized in suitable solvent like Isopropyl Alcohol and hexane mixture (6:94) to get 249 gm Pyraclostrobin having w/w % Purity 98.52% and Yield=96.0%

EXAMPLE 6

250 g of methyl [2-({[1-(4-chlorophenyl)-1-H-pyrazol-3-yl]oxy}methyl)phenyl]hydroxycarbamate is charged in 700 ml of Acetone. Then added 107 gm of Sodium Carbonate, 2.0 g of the Potassium Iodide is added; then the reaction flask is evacuated and with strong agitation, 46 g of methyl chloride is added as fast as possible at a temperature between 30°-50° C. Thereafter 32 minutes the required amount is absorbed. Maintained reaction mixture for 4.5 to 5.5 hrs at a reaction temperature in between 30°-50° C. under 3.0 to 5.0 Kg/cm$^2$ pressure. Thereafter the slurry is cooled to 25°-30° C. and the salt precipitate is isolated by filtration. Recovered solvent from mother liquor and product extracted in 100 ml Dichloromethane and given 100 ml water wash to the organic layer. After water washing recovered solvent from the organic layer to get crude Pyraclostrobin. Crude Pyraclostrobin then crystallized in suitable solvent like Isopropyl Alcohol and hexane mixture (7:93) to get 251.64 gm Pyraclostrobin having w/w % Purity=98.0% and Yield=97.02%

EXAMPLE 7

250 g of methyl [2-({[1-(4-chlorophenyl)-1-H-pyrazol-3-yl]oxy}methyl)phenyl]hydroxycarbamate is charged in 500 ml of 1,2-Dichloroethane. Then added 105 gm of Sodium Carbonate 3.0 g of the Potassium Iodide is added. Then the reaction flask is evacuated and with strong agitation. Then 50 of methyl chloride is added as fast as possible at a temperature between 30°-50° C. Thereafter in 32 minutes the required amount is absorbed. Maintained reaction mixture for 12 to 14 hrs at a reaction temperature of 30°-50° C. under 3.0 to 5.0 Kg/cm$^2$ pressure. Thereafter the slurry is cooled to 25°-30° C. and the salt precipitate is isolated by filtration. Filtrate washed with 100 ml water. After water washing recovered solvent from the organic layer to get crude Pyraclostrobin. Crude Pyraclostrobin then crystallized in a suitable solvent like Isopropyl Alcohol and hexane mixture (8:92) to get 246.40 gm Pyraclostrobin having w/w % Purity=97.02% and Yield=95.0%.

EXAMPLE 8

790 g of methyl [2-({[1-(4-chlorophenyl)-1-H-pyrazol-3-yl]oxy}methyl)phenyl]hydroxycarbamate is charged in 2400 ml of Butanone. Then added 310 gm of Potassium Carbonate, 10.0 g of the Potassium Iodide are added; then the reaction flask is evacuated and with strong agitation. 158 g of methyl chloride is added as fast as possible at a temperature between 30°-50° C. Thereafter in about 32 minutes the required amount is absorbed. Maintained reaction mixture for 10 to 12.0 hrs at a reaction temperature of 30°-50° C. under 3.0 to 5.0 Kg/cm$^2$ pressure. Thereafter the slurry is cooled to 25°-30° C. and the salt precipitate is isolated by filtration. Recovered solvent from the mother liquor and the product extracted in 100 ml Dichloromethane or Dichloromethane and given 100 ml water wash to the organic layer. After water washing recovered solvent from the organic layer to get crude Pyraclostrobin. Crude Pyraclostrobin then crystallized in a suitable solvent like Isopropyl Alcohol and hexane mixture (9:91) to get the high purity Pyraclostrobin having w/w % Purity 96.5% and Yield=95.0%.

EXAMPLE 9

250 g of methyl [2-({[1-(4-chlorophenyl)-1-H-pyrazol-3-yl]oxy}methyl)phenyl]hydroxycarbamate is charged in 750 ml of methyl tert-butyl ether. Then added 141 gm of Potassium Carbonate, 2.0 g of the Potassium Iodide is added. Then the reaction flask is evacuated and with strong agitation. Then 52 g of methyl chloride is added as fast as possible at a temperature between 30°-50° C. Thereafter in about 32 minutes the required amount is absorbed. Maintained reaction mixture for 6.0 to 7.0 hrs at a reaction temperature of 30°-50° under 3.0 to 6.0 Kg/cm$^2$ thereafter the slurry is cooled to 25°-30° C. and the salt precipitate is isolated by filtration. Filtrate (organic layer) wash with 100 ml water. After water washing recovered solvent from the organic layer to get crude Pyraclostrobin. Crude Pyraclostrobin then crystallized in suitable solvent like Polyethylene glycol PEG:Isopropyl Alcohol:hexane mixture (1:09:90) to get 256 gm Pyraclostrobin having w/w % Purity 98.70% and Yield=95.0%

COMPARATIVE DATA

Pyraclostrobin, Compound of Formula (I) Obtained by Methylation of methyl [2-({[1-(4-chlorophenyl)-1-H-pyrazol-3-yl]oxy}methyl)phenyl] hydroxycarbamate, Compound of Formula II.

|  | Methylating agent | Yield (%) | Purity (%) | Conversion rate(%) |
| --- | --- | --- | --- | --- |
| Present invention | Methyl Bromide | 95%-99% | 98%-99% | 99.80% |
|  | Methyl chloride | 95%-99% | 94%-99% | 97.89% |
| CN102399190 | Dimethyl Sulfate | 97%-98.5% | 95.2%-97.6% | Not mentioned |
| CN104211641 | Dimethyl Sulfate | 94.2% | 98.5 | Not mentioned |
|  | Dimethyl Carbonate | 93%-94% | 97.7%-98.7% | Not mentioned |
| CN105949125 | Dimethyl Sulfate | 94.9%-96.7% | 98%-98.7% | Not mentioned |
| CN106117143 | Dimethyl Sulfate | 89.6% | 96.3% | Not mentioned |
| CN105218450 | Dimethyl Sulfate | 86.74% to 89.96% | >98.0 | Not mentioned |
| CN104592117 | Dimethyl Sulfate | 88.3%-90.2% | 98.52%-98.83% | Not mentioned |
| U.S. Pat. No. 5869517 | Dimethyl Sulfate | 55% | Not mentioned | Not mentioned |

The invention claimed is:

1. An improved process for the preparation of methyl [2-({[1-(4-chlorophenyl)-1H-pyrazol-3-yl] oxy} methyl)phenyl]methoxycarbamate (Pyraclostrobin) of formula (I)

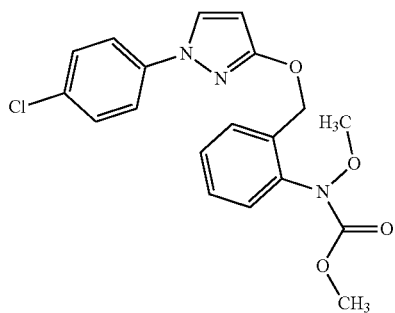

Formula(I)

comprising the steps of:

i) reacting compound of formula (II) with methylating agent selected from Methyl chloride or Methyl bromide in presence of a catalyst and acid binding agent selected from the group consisting of: Potassium Carbonate, Sodium Carbonate, Sodium Hydroxide, and Potassium Hydroxide in a solvent or mixture of solvents at a reaction temperature between 30°-50° C. at reduced pressure between 1.0 to 5.0 Kg/cm² to obtain crude Pyraclostrobin, compound of formula (I); and

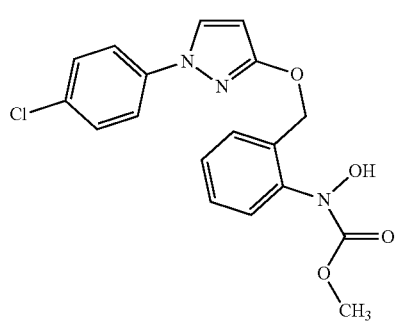

Formula(II)

ii) purifying the crude Pyraclostrobin of formula (I) obtained in step (i) in a suitable solvent or mixture of solvents.

2. The process as claimed in claim 1, wherein the methylating agent used in step (i) is Methyl chloride gas or Methyl bromide gas.

3. The process as claimed in claim 2, wherein the Mole ratio of methylating agent used for methylation reaction to the methyl[2-({[1-(4-chlorophenyl)-1H-pyrazol-3-yl]oxy}methyl)phenyl] hydroxycarbonate of formula (II) is in the range of 1 to 3.5.

4. The process as claimed in claim 1, wherein the reaction in step (i) is carried out in the presence of a catalyst that is Potassium Iodide and the ratio is 0.2 to 1.0% w/w on the basis of the methyl [2-({[1-(4-chlorophenyl)-1H-pyrazol-3-yl]oxy}methyl) phenyl] hydroxycarbamate of formula (II).

5. The process as claimed in claim 1, wherein the Mole Ratio of the acid binding agent to the methyl [2-({[1-(4-chlorophenyl)-1H-pyrazol-3-yl] oxy}methyl)phenyl]hydroxycarbamate of formula (II) is in the range of 1 to 1.5.

6. The process as claimed in claim 1, wherein the solvents used in step (i) are selected from acetone, methyl ethyl ketone, methyl isobutyl ketone, dichloromethane, dichloroethane, or mixture thereof.

7. The process as claimed in claim 1, wherein the solvent used in step (ii) for purifying the crude Pyraclostrobin obtained in step (i) is selected from Polyethylene glycol (PEG), Isopropyl Alcohol, hexane, or mixture thereof.

* * * * *

UNITED STATES PATENT AND TRADEMARK OFFICE
CERTIFICATE OF CORRECTION

PATENT NO. : 11,242,320 B2
APPLICATION NO. : 16/962542
DATED : February 8, 2022
INVENTOR(S) : Ajit Singh Gujral et al.

It is certified that error appears in the above-identified patent and that said Letters Patent is hereby corrected as shown below:

In the Claims

Column 14

Line 23, Claim 3:
Delete "methyl[2-({[1-(4-chlorophenyl)-1H-pyrazol-3-yl]oxy}methyl)phenyl]hydroxycarbonate" and insert --methyl[2-({[1-(4-chlorophenyl)-1-H-pyrazol-3-yl]oxy}methyl)phenyl]hydroxycarbamate--

Line 29, Claim 4:
Delete "methyl[2-({[1-(4-chlorophenyl)-1H-pyrazol-3-yl]oxy}methyl)phenyl]hydroxycarbamate" and insert --methyl[2-({[1-(4-chlorophenyl)-1-H-pyrazol-3-yl]oxy}methyl)phenyl]hydroxycarbamate--

Line 32, Claim 5:
Delete "methyl[2-({[1-(4-chlorophenyl)-1H-pyrazol-3-yl]oxy}methyl)phenyl]hydroxycarbamate" and insert --methyl[2-({[1-(4-chlorophenyl)-1-H-pyrazol-3-yl]oxy}methyl)phenyl]hydroxycarbamate--

Signed and Sealed this
Nineteenth Day of April, 2022

Katherine Kelly Vidal
*Director of the United States Patent and Trademark Office*